US009489934B2

(12) United States Patent
Song et al.

(10) Patent No.: US 9,489,934 B2
(45) Date of Patent: *Nov. 8, 2016

(54) METHOD FOR SELECTING MUSIC BASED ON FACE RECOGNITION, MUSIC SELECTING SYSTEM AND ELECTRONIC APPARATUS

(71) Applicant: National Chiao Tung University, Hsinchu (TW)

(72) Inventors: Kai-Tai Song, Hsinchu (TW); Chao-Yu Lin, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 282 days.

This patent is subject to a terminal disclaimer.

(21) Appl. No.: 14/284,405

(22) Filed: May 22, 2014

(65) Prior Publication Data

US 2015/0206523 A1    Jul. 23, 2015

(30) Foreign Application Priority Data

Jan. 23, 2014   (TW) .............................. 103102459 A

(51) Int. Cl.
*G06F 17/30* (2006.01)
*G06K 9/00* (2006.01)
(Continued)

(52) U.S. Cl.
CPC .............. *G10H 7/002* (2013.01); *A61B 5/0077* (2013.01); *A61B 5/165* (2013.01); *G10H 1/0008* (2013.01);
(Continued)

(58) Field of Classification Search
CPC ............. G06F 17/30; G06F 17/30023; G06F 17/30047; G06F 17/30053; G06F 17/30781; G06F 17/30784; G06F 17/3079; G06F 17/30823; G06F 17/30817; G06F 17/3084; G06K 9/00; G06K 9/00013; G06K 9/00221; G06K 9/00248; G06K 9/00268; G06K 9/00261; G06K 9/00302; G06K 9/00308; G06K 9/00315; G06K 9/00335; G06T 7/00
USPC .......... 84/600, 601, 615; 707/916, 705, 706, 707/736, 770, 769, 772, 776; 382/100, 118
See application file for complete search history.

(56) References Cited

U.S. PATENT DOCUMENTS 7,839,292 B2   11/2010  Wang et al.
8,094,891 B2    1/2012  Andreasson
(Continued)

FOREIGN PATENT DOCUMENTS

| CN | 101836219 | 9/2010 |
| TW | 201314586 | 4/2013 |
| TW | 201327226 | 7/2013 |

OTHER PUBLICATIONS

"Office Action of Taiwan Counterpart Application", issued on Jun. 29, 2015, p. 1-p. 9.
(Continued)

*Primary Examiner* — Paras D Shah
(74) *Attorney, Agent, or Firm* — Jianq Chyun IP Office

(57) ABSTRACT

A method for selecting music based on face recognition, a music selecting system and an electronic apparatus are provided. The method includes the following steps: accessing a database to retrieve a plurality of song emotion coordinates corresponding to a plurality of songs; mapping the song emotion coordinates to an emotion coordinate graph; capturing a human face image; identifying an emotion state corresponding to the human face image, and transforming the emotion state to a current emotion coordinate; mapping the current emotion coordinate to the emotion coordinate graph; updating a song playlist according to a relative position between the current emotion coordinate and a target emotion coordinate, wherein the song playlist includes a plurality of songs to be played that direct the current emotion coordinate to the target emotion coordinate.

7 Claims, 14 Drawing Sheets

(51) Int. Cl.
  *G10H 7/00* (2006.01)
  *A61B 5/16* (2006.01)
  *A61B 5/00* (2006.01)
  *G10H 1/00* (2006.01)

(52) U.S. Cl.
  CPC ... *G06F 17/30026* (2013.01); *G06F 17/30047* (2013.01); *G06K 9/00221* (2013.01); *G10H 2220/131* (2013.01); *G10H 2220/455* (2013.01); *G10H 2240/085* (2013.01); *G10H 2240/131* (2013.01); *G10H 2240/141* (2013.01); *G10H 2250/131* (2013.01)

(56) References Cited

U.S. PATENT DOCUMENTS

| | | | |
|---|---|---|---|
| 8,102,417 | B2 | 1/2012 | Hammoud et al. |
| 8,407,055 | B2* | 3/2013 | Asano et al. ............. 704/270 |
| 8,489,606 | B2* | 7/2013 | Lee et al. ............... 707/738 |
| 2004/0237759 | A1* | 12/2004 | Bill ....................... 84/668 |
| 2006/0054007 | A1* | 3/2006 | Lu et al. ................. 84/611 |
| 2006/0143647 | A1* | 6/2006 | Bill ....................... 725/10 |
| 2007/0131095 | A1* | 6/2007 | Park et al. ............... 84/609 |
| 2007/0157795 | A1* | 7/2007 | Hung ..................... 84/600 |
| 2008/0189331 | A1* | 8/2008 | Lee et al. ............... 707/104.1 |
| 2009/0069914 | A1* | 3/2009 | Kemp ................. G10H 1/0008 700/94 |
| 2010/0053168 | A1* | 3/2010 | Kemp ............... G06F 17/30017 345/440 |
| 2010/0063880 | A1* | 3/2010 | Atsmon et al. ........... 705/14.53 |
| 2011/0283190 | A1* | 11/2011 | Poltorak .................. 715/716 |
| 2011/0289075 | A1* | 11/2011 | Nelson ................... 707/723 |
| 2011/0310237 | A1 | 12/2011 | Wang et al. |
| 2013/0132988 | A1* | 5/2013 | Lee .................. H04N 21/4394 725/14 |
| 2013/0138684 | A1* | 5/2013 | Kim et al. ............... 707/769 |
| 2013/0268273 | A1* | 10/2013 | Chen et al. .............. 704/249 |
| 2014/0052731 | A1* | 2/2014 | Dahule et al. ........... 707/740 |

OTHER PUBLICATIONS

Yoon et al, "Music Recommendation System Using Emotion Triggering Low-level Features," IEEE Transactions on Consumer Electronics, May 2012, pp. 612-618.

Yang et al., "Mr. Emo: Music Retrieval in the Emotion Plane," MM '08 Proceedings of the 16th ACM international conference on Multimedia, Oct. 2008, pp. 1003-1004.

Chao-Yu Lin, "Robust Emotion Recognition by Using a Temporal-Reinforced Approach," Thesis of Master degree, College of Electrical and Computer Engineering National Chiao Tung University, Jul. 2013, pp. 1-112.

* cited by examiner

METHOD FOR SELECTING MUSIC BASED ON FACE RECOGNITION, MUSIC SELECTING SYSTEM AND ELECTRONIC APPARATUS

CROSS-REFERENCE TO RELATED APPLICATION

This application claims the priority benefit of Taiwan application serial no. 103102459, filed on Jan. 23, 2014. The entirety of the above-mentioned patent application is hereby incorporated by reference herein and made a part of this specification.

BACKGROUND

1. Technical Field

The invention relates to a method for selecting music, a music selecting system and an electronic apparatus. Particularly, the invention relates to a method for selecting music based on face recognition, a music selecting system and an electronic apparatus.

2. Related Art

U.S. Pat. No. 8,094,891 provides a method for selecting and playing music, by which an emotion type of a user is recognized according to a captured face image of the user, and corresponding music is played with reference of a music feature. According to such invention, a song playlist is determined through one-off determination on user's emotion and music type without considering a possible emotion change of the user during a music playing process. Namely, the song playlist of the invention is not changed after it is generated, and the content of the song playlist cannot be adjusted according to the emotion change of the user.

U.S. Pat. No. 8,489,606 provides a method for selecting music, by which songs to be played are determined according to an emotion type specified by the user. A music selecting system of the invention recognizes a graph input by the user to determine an emotion type of the graph and an arousal-valence (A-V) range corresponding to the emotion type, and accordingly obtains several corresponding music A-V to create a song playlist. According to the such invention, the user has to express the personal emotion through a graph, and the system recognizes the corresponding A-V according to information of the graph (for example, a shape, a size) drawn by the user, so as to select several suitable songs to create the song playlist for playing. However, during the song playing process, the invention is lack of consideration on user's emotion change and changing of user's emotion.

U.S. Pat. No. 7,839,292 provides a method and a system for predicting dangerous driving. In the invention, a sequence learning algorithm is used to determine vehicle dynamic parameters and capture driver physiological data, driver behavior and state characteristics to predict dangerous driving and assist the driver to drive safely. In such invention, a sound warning device is used to alert the driver performing the dangerous driving. However, such sound warning system that suddenly produces devastating sound alert may cause unexpected accident.

U.S. Pat. No. 8,102,417 provides a method for recognizing a closing state of driver's eyes. In the invention, a video capturing device is used to capture an image of an eye area of the driver, and a video processor is used to determine whether the image of the eye area is a noise, i.e. whether an eye ball is detected, and after some determinations on open and close variations of the eyes for a period of time, it is determined whether the driver conducts fatigue driving. According to such invention, only the determination on driver's state is performed in allusion to the eye area, which is mainly used for fatigue recognition. However, regarding a driver's emotion, whether the driver's emotion is under control is still required to be considered.

SUMMARY

The invention provides a method for selecting music based on face recognition, which is adapted to a music selecting system. The method includes the following steps. A database is accessed to retrieve a plurality of song emotion coordinates corresponding to a plurality of songs. The song emotion coordinates are mapped to an emotion coordinate graph. A human face image is captured. An emotion state corresponding to the human face image is recognized, and the emotion state is transformed to a current emotion coordinate. The current emotion coordinate is mapped to the emotion coordinate graph. A song playlist is updated according to a relative position between the current emotion coordinate and a target emotion coordinate, where the song playlist includes a plurality of songs to be played that direct the current emotion coordinate to the target emotion coordinate.

In an embodiment of the invention, the step of updating the song playlist according to the relative position between the current emotion coordinate and the target emotion coordinate includes the following steps. A plurality of reference emotion coordinates are defined on a first connection line, where the first connection line is connected between the current emotion coordinate and the target emotion coordinate. A plurality of candidate song emotion coordinates closest to the reference emotion coordinates are selected from the song emotion coordinates. The songs corresponding to the candidate song emotion coordinates are set to be the songs to be played.

In an embodiment of the invention, the step of defining the reference emotion coordinates on the first connection line includes a following step. An $n^{th}$ reference emotion coordinate in the reference emotion coordinates is characterized as:

$$A_E^n = A_S + \frac{d_{TS}}{N_R} \times \sin(\theta_{TS}) \times n,$$

$$V_E^n = V_S + \frac{d_{TS}}{N_R} \times \cos(\theta_{TS}) \times n,$$

where, $N_R$ is a total number of the songs to be played, n is a positive integer between 1 and $N_R$, $d_{TS}$ is a distance between the emotion coordinate and the target emotion coordinate, $\theta_{TS}$ is an included angle between a horizontal axis of the emotion coordinate graph and the first connection line, $A_E^n$ is a vertical coordinate of the $n^{th}$ reference emotion coordinate on the emotion coordinate graph, $V_E^n$ is a horizontal coordinate of the $n^{th}$ reference emotion coordinate on the emotion coordinate graph, $A_S$ is a vertical coordinate of the current emotion coordinate on the emotion coordinate graph, and $V_S$ is a horizontal coordinate of the current emotion coordinate on the emotion coordinate graph.

In an embodiment of the invention, an $n^{th}$ candidate song emotion coordinate in the candidate song emotion coordinates satisfies a following equation:

$$(V_M^n, A_M^n) = \arg \min_{V_M, A_M} \left( \sqrt{(V_E^n - V_M)^2 + (A_E^n - A_M)^2} \times w \right),$$

where, $A_M^n$ is a vertical coordinate of an $n^{th}$ candidate song emotion coordinate on the emotion coordinate graph, $V_M^n$ is a horizontal coordinate of the $n^{th}$ candidate song emotion coordinate on the emotion coordinate graph, $$w = \frac{1}{\cos(\theta_{EM}) + 2},$$

$\theta_{EM}$ is an included angle between a second connection line and a third connection line, where the second connection line is connected between the $n^{th}$ reference emotion coordinate and the target emotion coordinate, and the third connection line is connected between the $n^{th}$ reference emotion coordinate and the $n^{th}$ candidate song emotion coordinate.

In an embodiment of the invention, after the step of updating the song playlist according to the relative position between the current emotion coordinate and the target emotion coordinate, the method further includes a following step. The songs to be played are played according to the song playlist.

In an embodiment of the invention, after the step of playing the songs to be played according to the song playlist, the method further includes following steps. The steps of capturing the human face image, recognizing the emotion state corresponding to the human face image, mapping the current emotion coordinate to the emotion coordinate graph and updating the song playlist according to the relative position between the current emotion coordinate and the target emotion coordinate are repeated until the current emotion coordinate is directed to the target emotion coordinate or playing of the songs to be played is finished.

The invention provides a music selecting system including an image capturing device, an image processing device, a control device, a playing device and a database. The image processing device is connected to the image capturing device. The control device is connected to the image processing device. The playing device is connected to the control device. The database is connected to the control device. The control device accesses the database to retrieve a plurality of song emotion coordinates corresponding to a plurality of songs. The control device maps the song emotion coordinates to an emotion coordinate graph. The image capturing device captures a human face image. The image processing device recognizes an emotion state corresponding to the human face image, and transforms the emotion state to a current emotion coordinate. The control device maps the current emotion coordinate to the emotion coordinate graph. The control device updates a song playlist according to a relative position between the current emotion coordinate and a target emotion coordinate, where the song playlist includes a plurality of songs to be played that direct the current emotion coordinate to the target emotion coordinate.

In an embodiment of the invention, the control device defines a plurality of reference emotion coordinates on a first connection line, where the first connection line is connected between the current emotion coordinate and the target emotion coordinate, selects a plurality of candidate song emotion coordinates closest to the reference emotion coordinates from the song emotion coordinates, and sets the songs corresponding to the candidate song emotion coordinates to be the songs to be played.

In an embodiment of the invention, the control device characterizes an $n^{th}$ reference emotion coordinate in the reference emotion coordinates as:

$$A_E^n = A_S + \frac{d_{TS}}{N_R} \times \sin(\theta_{TS}) \times n,$$

$$V_E^n = V_S + \frac{d_{TS}}{N_R} \times \cos(\theta_{TS}) \times n,$$

where, $N_R$ is a total number of the songs to be played, $n$ is a positive integer between 1 and $N_R$, $d_{TS}$ is a distance between the emotion coordinate and the target emotion coordinate, $\theta_{TS}$ is an included angle between a horizontal axis of the emotion coordinate graph and the first connection line, $A_E^n$ is a vertical coordinate of the $n^{th}$ reference emotion coordinate on the emotion coordinate graph, $V_E^n$ is a horizontal coordinate of the $n^{th}$ reference emotion coordinate on the emotion coordinate graph, $A_S$ is a vertical coordinate of the current emotion coordinate on the emotion coordinate graph, and $V_S$ is a horizontal coordinate of the current emotion coordinate on the emotion coordinate graph.

In an embodiment of the invention, an $n^{th}$ candidate song emotion coordinate in the candidate song emotion coordinates satisfies a following equation:

$$(V_M^n, A_M^n) = \arg \min_{V_M, A_M} \left( \sqrt{(V_E^n - V_M)^2 + (A_E^n - A_M)^2} \times w \right),$$

where, $A_M^n$ is a vertical coordinate of an $n^{th}$ candidate song emotion coordinate on the emotion coordinate graph, $V_M^n$ is a horizontal coordinate of the $n^{th}$ candidate song emotion coordinate on the emotion coordinate graph, $$w = \frac{1}{\cos(\theta_{EM}) + 2},$$

$\theta_{EM}$ is an included angle between a second connection line and a third connection line, where the second connection line is connected between the $n^{th}$ reference emotion coordinate and the target emotion coordinate, and the third connection line is connected between the $n^{th}$ reference emotion coordinate and the $n^{th}$ candidate song emotion coordinate.

In an embodiment of the invention, the playing device plays the songs to be played according to the song playlist.

The invention provides an electronic apparatus including an image capturing device, an image processing device, a control device, a playing device and a database. The image processing device is connected to the image capturing device. The control device is connected to the image processing device. The playing device is connected to the control device. The database is connected to the control device. The control device accesses the database to retrieve a plurality of song emotion coordinates corresponding to a plurality of songs. The control device maps the song emotion coordinates to an emotion coordinate graph. The image capturing device captures a human face image. The image processing device recognizes an emotion state corresponding to the human face image, and transforms the emotion state to a current emotion coordinate. The control device maps the current emotion coordinate to the emotion coordinate graph. The control device updates a song playlist according to a relative position between the current emotion coordinate and a target emotion coordinate, where the song playlist includes a plurality of songs to be played that direct the current emotion coordinate to the target emotion coordinate.

According to the above descriptions, according to the method for selecting music based on face recognition, the music selecting system and the electronic apparatus of the invention, after the emotion state is recognized based on the human face image, the songs to be played to the user are controlled by adjusting the song playlist.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
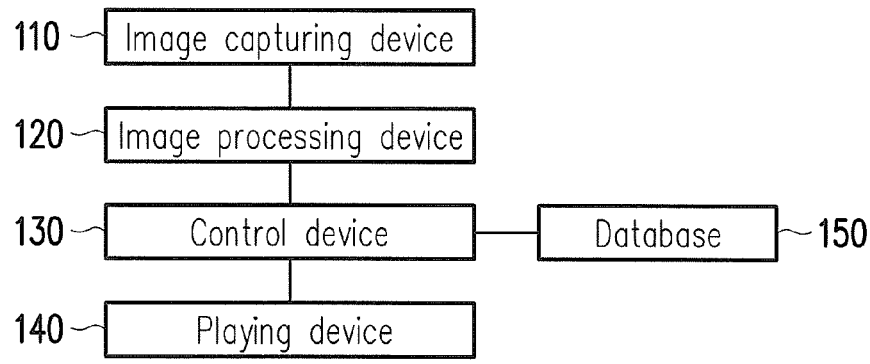
FIG. 1 is a schematic diagram of a music selecting system according to an embodiment of the invention.

FIG. 1 is a schematic diagram of a music selecting system according to an embodiment of the invention. In the present embodiment, the music selecting system 100 includes an image capturing device 110, an image processing device 120, a control device 130, a playing device 140 and a database 150. The image capturing device 110 is connected to the image processing device 120. The control device 130 is connected to the image processing device 120, the playing device 140 and the database 150.

The image capturing device 110 is, for example, any camera having a charge coupled device (CCD) lens, a complementary metal oxide semiconductor transistor (CMOS) lens, or an infrared lens, and can also be an image capturing device capable of obtaining depth information, for example, a depth camera or a stereo camera, and as long as the applied image capturing device is capable of capturing images, it is considered to be within the scope of the present invention.

The image processing device 120 can be a hardware device such as an image processing chip, a processor or a computer system, etc., or can be a software module having an image processing function (for example, an application capable of recognizing, capturing or editing images). Moreover, the image processing device 120 can be a combination of hardware and software devices.

The control device 130 can be a function module implemented by hardware and/or software. The hardware may include a hardware device having a computing function, such as a central processor, a chipset, a microprocessor, etc., or a combination thereof, and the software can be an operating system, a driving program, etc. The playing device 140 can be a general music player, for example, a sound system, etc. The database 150 can be a memory in an electronic apparatus or a network server storing song files, etc.

In an embodiment, the music selecting system 100 of the invention can be implemented in an electronic apparatus such as a smart phone, a tablet personal computer (PC), a desktop computer, a notebook computer, etc. In other embodiment, various devices of the music selecting system 100 can also be implemented as a plurality of independent electronic apparatuses, and the electronic apparatuses can cooperate to implement various characteristics and effects introduced in the following embodiments, though the invention is not limited thereto.

Schematically, in the method of the invention, after an emotion state of the user is recognized based on a human face image, songs to be played to the user are controlled by adjusting a song playlist, so as to gradually direct the emotion state of the user (for example, nervous, tired, angry and sad, etc.) to a target emotion state (for example, relaxed, pleased and happy, etc.). Details of the method of the invention are introduced below.

Figure 2:
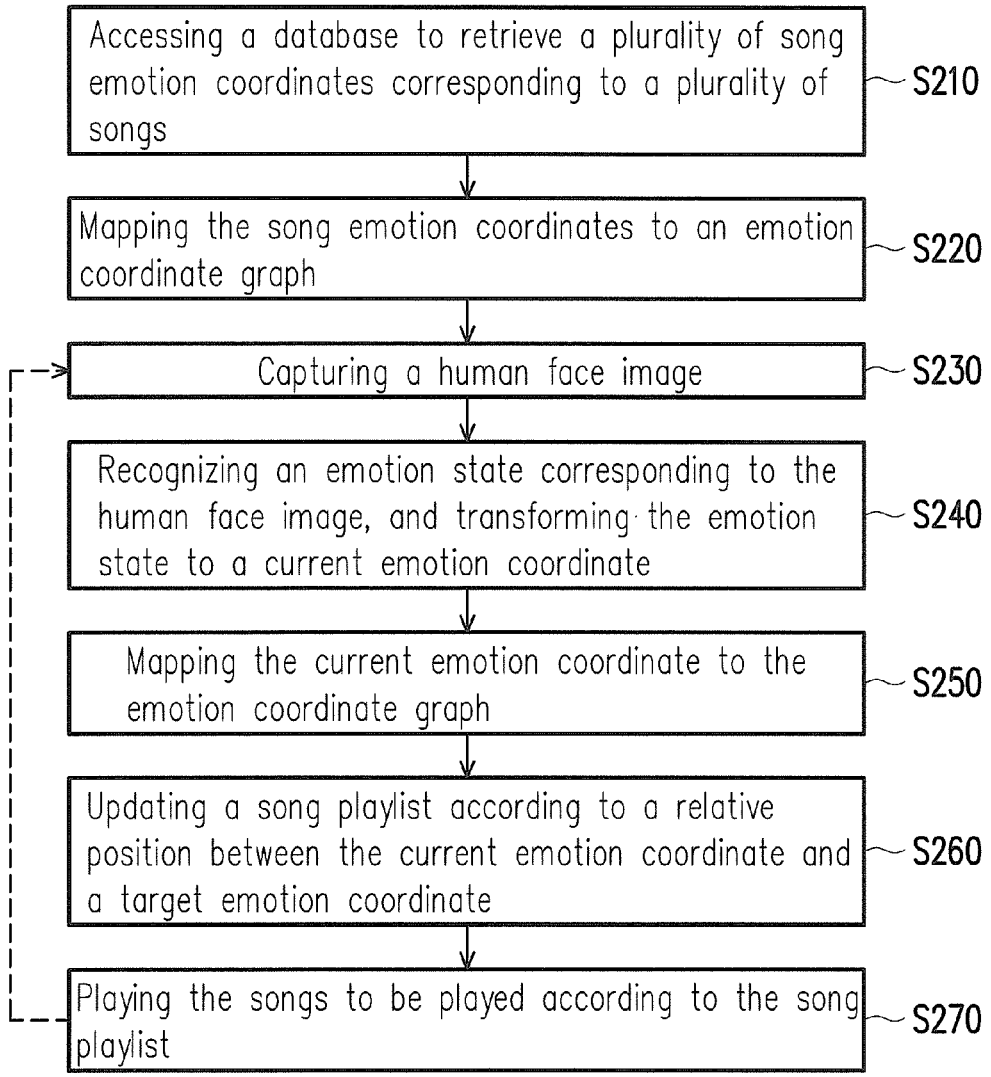
FIG. 2 is a flowchart illustrating a method for selecting music based on face recognition according to an embodiment of the invention.

FIG. 2 is a flowchart illustrating a method for selecting music based on face recognition according to an embodiment of the invention. The method of the invention can be executed by the music selecting system 100 of FIG. 1, and detailed steps of the method are introduced below with reference of various devices shown in FIG. 1.

In step S210, the control device 130 accesses the database 150 to retrieve a plurality of song emotion coordinates corresponding to a plurality of songs. In step S220, the control device 130 maps the song emotion coordinates to an emotion coordinate graph.

Figure 3A:
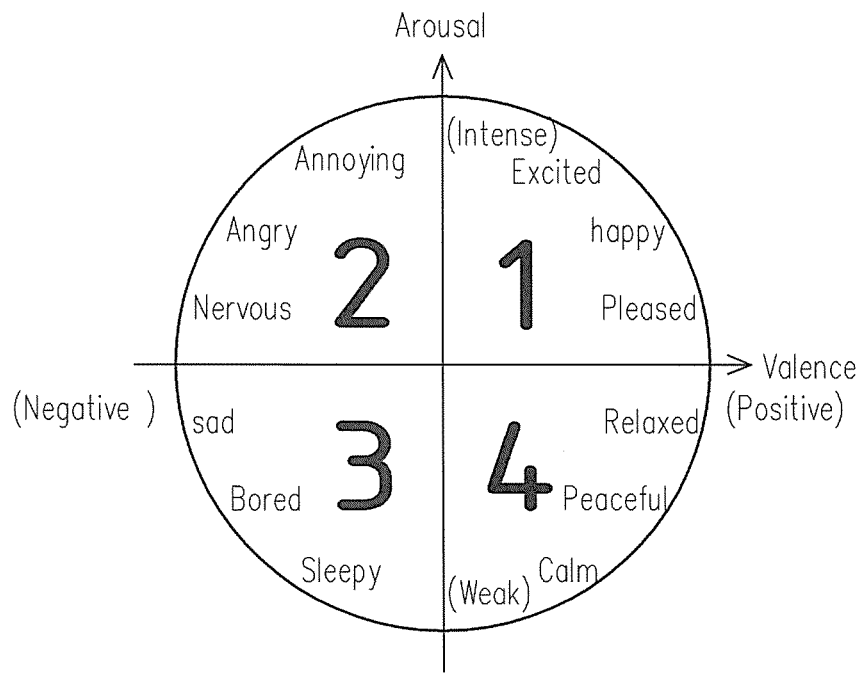
FIG. 3A is a schematic diagram of a two-dimensional emotional plane based on psychology.

The aforementioned emotion coordinate graph is defined according to a two-dimensional emotional plane provided by a psychologist Thayer. Referring to FIG. 3A, FIG. 3A is a schematic diagram of a two-dimensional emotional plane based on psychology. The psychologist Thayer provides the emotional plane shown in FIG. 3A. An X-axis of FIG. 3A represents valence of emotion, which is positive rightwards and is negative leftwards, and a Y-axis represents arousal of emotion, which is high upwards and low downwards. Different kinds of emotions are defined in FIG. 3A, for example, excited, happy, pleased, relaxed, peaceful, calm, sleepy, bored, sad, nervous, angry, annoying, etc.

Figure 3B:
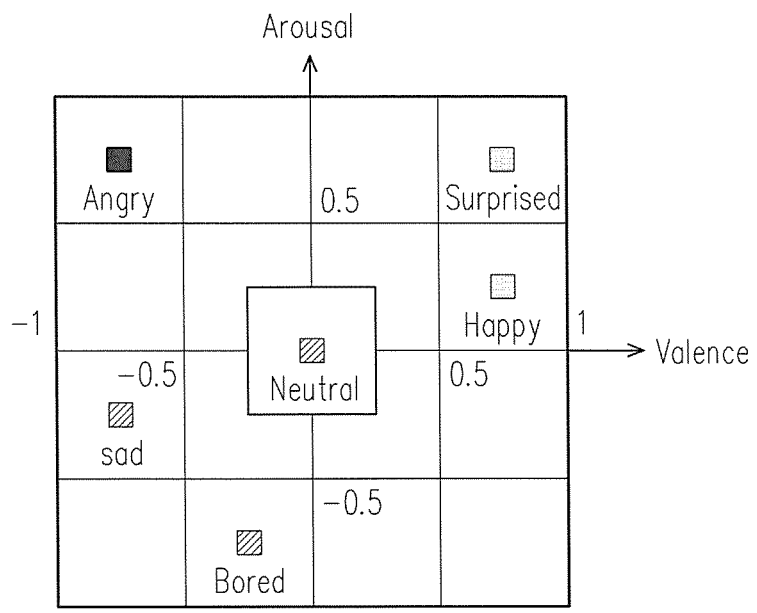
FIG. 3B is an emotion coordinate graph according to an embodiment of the invention.

FIG. 3B is an emotion coordinate graph according to an embodiment of the invention. Based on the theoretical basis shown in FIG. 3A, in the emotion coordinate graph, the X-axis represents the valance of emotion, where the maximum value of the X-axis is defined to be +1, and the minimum value thereof is defined to be −1. The Y-axis represents the arousal of emotion, where the maximum value of the Y-axis is defined to be +1, and the minimum value thereof is defined to be −1. In the emotion coordinate graph, a central region is defined as a neutral emotion, and other regions of the emotion coordinate graph is defined into emotions of pleasantly surprised, happy, bored, sad, angry, etc.

Figure 4:
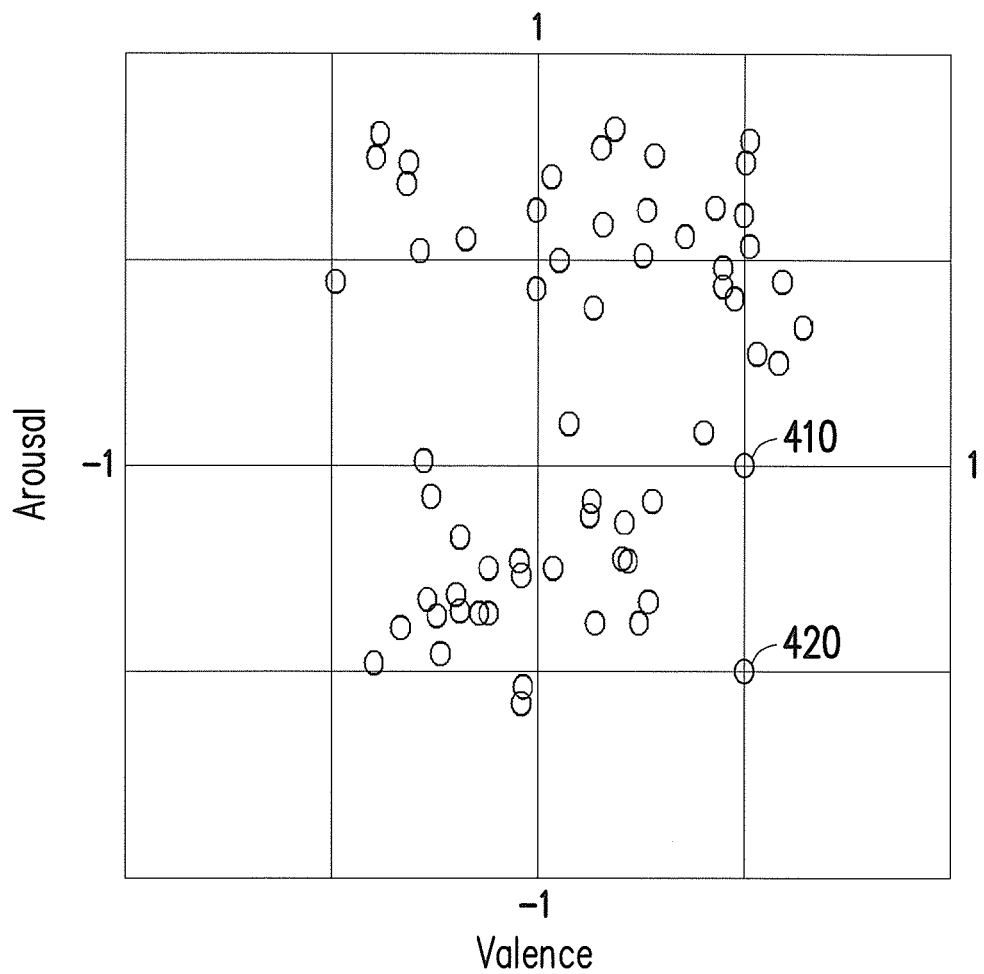
FIG. 4 is a schematic diagram of mapping song emotion coordinates to the emotion coordinate graph.

Referring to FIG. 4, FIG. 4 is a schematic diagram of mapping the song emotion coordinates to the emotion coordinate graph. In the present embodiment, each song in the database 150 may have a corresponding song emotion coordinate (which is represented by circles in FIG. 4) according to an individual music type thereof. The song emotion coordinates can be manually input to the database 150 or can be automatically produced by analysing rhythm, melody and arrangement of the songs through a specific system.

It should be noticed that each of the song emotion coordinates shown in FIG. 4 can be presented in form of (V, A) according to a position thereof in the emotion coordinate graph, where V represents a horizontal coordinate of the song emotion coordinate, and A represents a vertical coordinate of the song emotion coordinate. Taking a song emotion coordinate 410 as an example, it can be represented as (0.5, 0), where 0.5 is the horizontal coordinate of the song emotion coordinate 410, and 0 is the vertical coordinate of the song emotion coordinate 410. Taking a song emotion coordinate 420 as an example, it can be represented as (0.5, −0.5), where 0.5 is the horizontal coordinate of the song emotion coordinate 420, and −0.5 is the vertical coordinate of the song emotion coordinate 420. The (V, A) values corresponding to the other song emotion coordinates in FIG. 4 can be deduced according to the above instructions, which are not repeated.

Referring to FIG. 2 again, in step S230, the image capturing device 110 captures a human face image. In an embodiment, the image capturing device 110 can be disposed at a position suitable for continually capturing images of the user's face when the user conducts a specific behaviour, so as to capture the human face image of the user. In other embodiments, when the image capturing device 110 captures an image, the image processing device 120 can execute a general human face recognition algorithm to find out a human face existed in the image. Moreover, the image processing device 120 can further normalize the human face image, such that influences of a background noise and a size of the human face are avoided when characteristics of the human face are analysed later. In detail, it is assumed that the image captured by the image capturing device 110 is 640× 480, the image processing device 120 can normalize the image into 200×240, though the invention is not limited thereto.

Then, in step S240, the image processing device 120 recognizes an emotion state corresponding to the human face image, and transforms the emotion state to a current emotion coordinate. In an embodiment, the image processing device 120 can obtain an expression corresponding to the human face image based on, for example, an active appearance model (AAM) algorithm. In detail, the image processing device 120 can detect a plurality of characteristic points in the human face image. The characteristic points are, for example, respectively located at eyebrows, nose, eyes contour, face contour, mouth outer edge and mouth inner edge of the human face, though the invention is not limited thereto.

Thereafter, the image processing device 120 can capture geometric characteristics such as a distance characteristic and a displacement characteristic between the characteristic points.

Then, the image processing device 120 can recognize the emotion state corresponding to the geometric characteristics through a relevance vector machine (RVM) classifier. The emotion state is, for example, an emotion likelihood. In other embodiments, when the image processing device 120 recognizes the emotion likelihood, the image processing device 120 can take a previously recognized emotion likelihood (corresponding to a previously captured human face image) into consideration. In this way, when the user is transformed from a first emotion into a second emotion, the image processing device 120 can continuously recognize the emotion transformation process to ensure reasonableness and correctness of such process. In detail, the image processing device 120 can suppress wrong judgement on the emotion likelihood and unreasonable instant emotion transformation.

Moreover, the image processing device 120 can analyse the emotion likelihood based on a RVM regression model, and transform the emotion likelihood into the corresponding current emotion coordinate. Similar to the aforementioned song emotion coordinates, the current emotion coordinate can also be represented in form of corresponding (V, A).

Then, in step S250, the control device 130 maps the current emotion coordinate to the emotion coordinate graph. Namely, the control device 130 defines a position corresponding to the emotion state on the emotion coordinate graph according to the current emotion coordinate. The song playlist includes a plurality of songs to be played that direct the current emotion coordinate to the target emotion coordinate.

In step S260, the control device 130 updates the song playlist according to a relative position between the current emotion coordinate and a target emotion coordinate.

Figure 5:
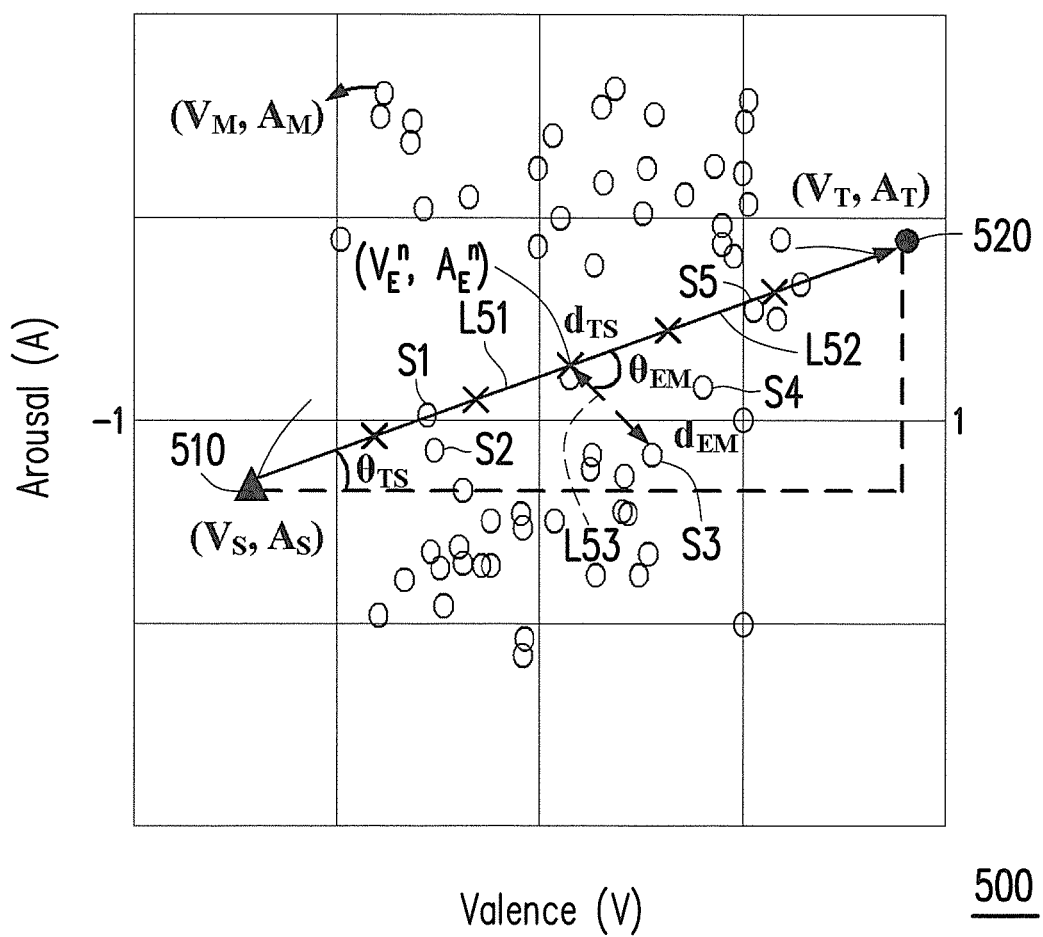
FIG. 5 is an emotion coordinate graph according to an embodiment of the invention.

Referring to FIG. 5, FIG. 5 is an emotion coordinate graph according to an embodiment of the invention. It is assumed that a current emotion coordinate 510 is the current emotion coordinate mapped to the emotion coordinate graph by the control device 130 after executing the step S250, and a target emotion coordinate 520 is a current emotion coordinate corresponding to the target emotion state (for example, happy). In the present embodiment, a position of the current emotion coordinate 510 in the emotion coordinate graph 500 indicates that the current emotion state of the user is close to an emotion of sad. The current emotion coordinate 510 can be represented as $(V_S, A_S)$, and the target emotion coordinate 520 can be represented as $(V_T, A_T)$. $A_S$ is a vertical coordinate of the current emotion coordinate 510 on the emotion coordinate graph 500, and $V_S$ is a horizontal coordinate of the current emotion coordinate 510 on the emotion coordinate graph 500. Moreover, each of the song emotion coordinate can be schematically represented as $(V_M, A_M)$.

In the present embodiment, the control device 130 defines a plurality of reference emotion coordinates on a first connection line L51, where the first connection line L51 is connected between the current emotion coordinate 510 and the target emotion coordinate 520. In detail, the control device 130 characterizes an $n^{th}$ reference emotion coordinate in the reference emotion coordinates as:

$$A_E^n = A_S + \frac{d_{TS}}{N_R} \times \sin(\theta_{TS}) \times n,$$

$$V_E^n = V_S + \frac{d_{TS}}{N_R} \times \cos(\theta_{TS}) \times n,$$

where $N_R$ is a total number of the songs to be played, n is a positive integer between 1 and $N_R$, $d_{TS}$ is a distance between the current emotion coordinate 510 and the target emotion coordinate 520, $\theta_{TS}$ is an included angle between a horizontal axis of the emotion coordinate graph 500 and the first connection line L51, $A_E^n$ is a vertical coordinate of the n<sup>th</sup> reference emotion coordinate on the emotion coordinate graph 500, $V_E^n$ is a horizontal coordinate of the n<sup>th</sup> reference emotion coordinate on the emotion coordinate graph 500.

After defining the reference emotion coordinates, the control device 130 selects a plurality of candidate song emotion coordinates closest to the reference emotion coordinates from the song emotion coordinates. In detail, the control device 130 can find song emotion coordinates satisfying a specific condition from a plurality of song emotion coordinates, and defines the song emotion coordinates as the candidate song emotion coordinates.

For example, an n<sup>th</sup> candidate song emotion coordinate in the candidate song emotion coordinates satisfies a following equation:

$$(V_M^n, A_M^n) = \arg \min_{V_M, A_M} \left( \sqrt{(V_E^n - V_M)^2 + (A_E^n - A_M)^2} \times w \right),$$

where $A_M^n$ is a vertical coordinate of an n<sup>th</sup> candidate song emotion coordinate on the emotion coordinate graph, $V_M^n$ is a horizontal coordinate of the n<sup>th</sup> candidate song emotion coordinate on the emotion coordinate graph, $$w = \frac{1}{\cos(\theta_{EM}) + 2},$$

$\theta_{EM}$ is an included angle between a second connection line L52 and a third connection line L53. The second connection line L52 is connected between the n<sup>th</sup> reference emotion coordinate and the target emotion coordinate 520, and the third connection line L53 is connected between the n<sup>th</sup> reference emotion coordinate and the n<sup>th</sup> candidate song emotion coordinate.

After defining the candidate song emotion coordinates, the control device 130 sets the songs corresponding to the candidate song emotion coordinates to be the songs to be played.

In the present embodiment, it is assumed that $N_R$ is 5, i.e. the total number of the songs to be played in the song playlist is 5. Therefore, the control device 130 sequentially defines song emotion coordinates S1-S5 that satisfy the aforementioned specific condition to be a first to a fifth candidate song emotion coordinates base on the aforementioned instructions. Then, the control device 130 sets the songs corresponding to the song emotion coordinates S1-S5 as the songs to be played in the song playlist.

Referring to FIG. 2 again, in step S270, the playing device 140 plays the songs to be played according to the song playlist. In this way, when the user listens to the songs played by the playing device 140, the music selecting system 100 can gradually direct the current emotion coordinate (i.e. the emotion state) of the user to the target emotion coordinate, so as to achieve an effect of improving the user's emotion through the songs.

Taking FIG. 5 as an example, when the user sequentially listens to the songs corresponding to the song emotion coordinates S1-S5, the emotion state of the use can be gradually directed from the emotion of sad (corresponding to the current emotion coordinate 510) to the emotion of happy (corresponding to the target emotion coordinate 520).

However, since the emotion state of the user is probably not ideally changed along with the played songs, in other embodiments, after the step S260, the music selecting system 100 can execute the steps S230-S260 again to repeatedly capture the human face images of the user to track the emotion states of the user. Moreover, the music selecting system 100 can adaptively update the songs to be played in the song playlist according to the emotion state recognized each time until the current emotion coordinate is directed to the target emotion coordinate or playing of the songs to be played is finished. Namely, the music selecting system 100 can repeatedly execute the steps S230-S260 until the number of the played songs reaches the total number of the songs to be played (i.e. $N_R$), or until the emotion state of the user is close to the target emotion state.

Figure 6:
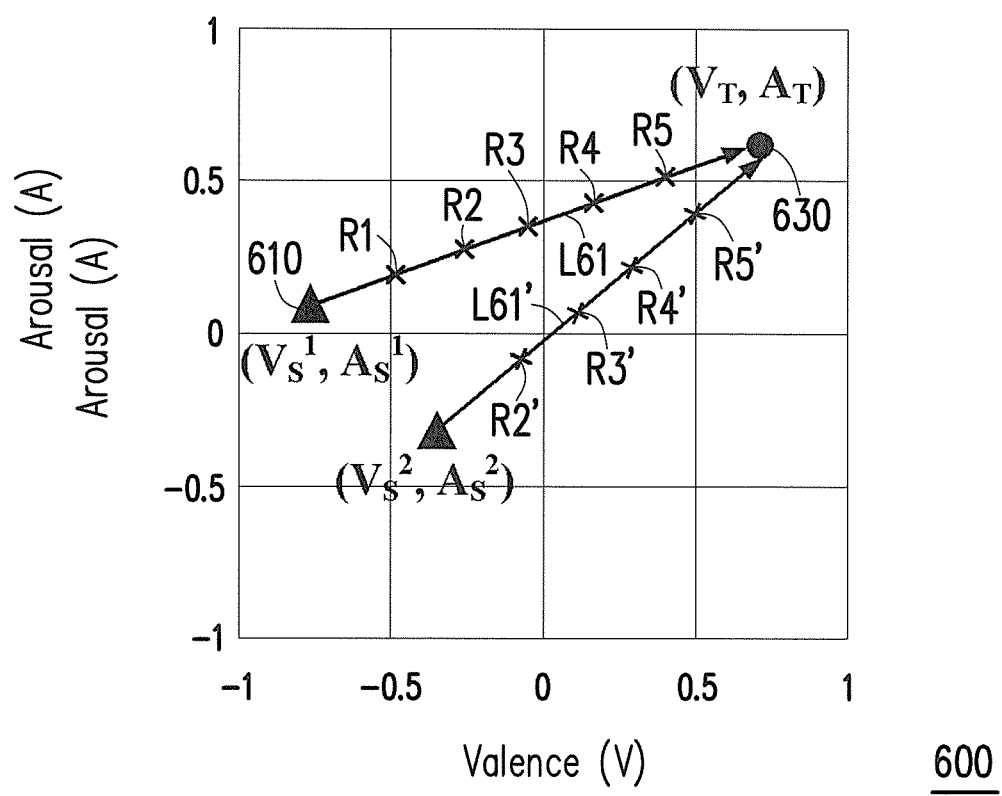
FIG. 6 is a schematic diagram of updating songs to be played according to an embodiment of the invention.

Referring to FIG. 6, FIG. 6 is a schematic diagram of updating the songs to be played according to an embodiment of the invention. In the present embodiment, it is assumed that a current emotion coordinate 610 corresponds to the emotion state of a first recognition, which is represented as $(V_S^1, A_S^1)$. Therefore, when the control device 130 executes the step S260 according to the aforementioned instructions, the control device 130 defines reference emotion coordinates R1-R5 on a first connection line L61 connected between the current emotion coordinate 610 and a target emotion coordinate 630 (which is represented as $(V_T, A_T)$). Then, the control device 130 selects a plurality of candidate song emotion coordinates (not shown) closest to the reference emotion coordinates R1-R5 from a plurality of the song emotion coordinates (not shown) in the emotion coordinate graph 600, and sets the songs corresponding to the candidate song emotion coordinates as the songs to be played.

As described above, the music selecting system 100 can repeatedly execute the steps S230-S260 to capture the human face images of the user to track the emotion states of the user. Therefore, when the current emotion coordinate corresponding to the emotion state of a second recognition is a current emotion coordinate 620 (which is represented as $(V_S^2, A_S^2)$), the control device 130 defines reference emotion coordinates R2'-R5' on a first connection line L61' connected between the current emotion coordinate 620 and the target emotion coordinate 630. Then, the control device 130 selects a plurality of candidate song emotion coordinates (not shown) closest to the reference emotion coordinates R2'-R5' from a plurality of the song emotion coordinates (not shown) in the emotion coordinate graph 600, and updates the song playlist according to the songs corresponding to the candidate song emotion coordinates.

In detail, it is assumed that the songs to be played that are selected by the control device 130 according to the current emotion coordinate 610 are songs AA-EE (individually corresponding to the reference emotion coordinates R1-R5). In this case, the playing device 140 can sequentially play the songs AA-EE. However, when the current emotion coordinate corresponding to the emotion state of the second recognition of the music selecting system 100 is the current emotion coordinate 620, since the playing device 140 is probably playing the song AA, the control device 130 may update the songs BB-EE to songs BB'-EE' according to the reference emotion coordinates R2'-R5'. Namely, the control device 130 only adjusts the songs that are not yet played in the song playlist.

Moreover, in an embodiment, it is assumed that after the playing device 140 finishes playing the song AA, if the emotion state of the user that is recognized by the music selecting system 100 is not changed, the playing device 140 continually plays the song BB, so as to direct the emotion state of the user through the songs closer to the target emotion coordinate 630.

Figure 7A:
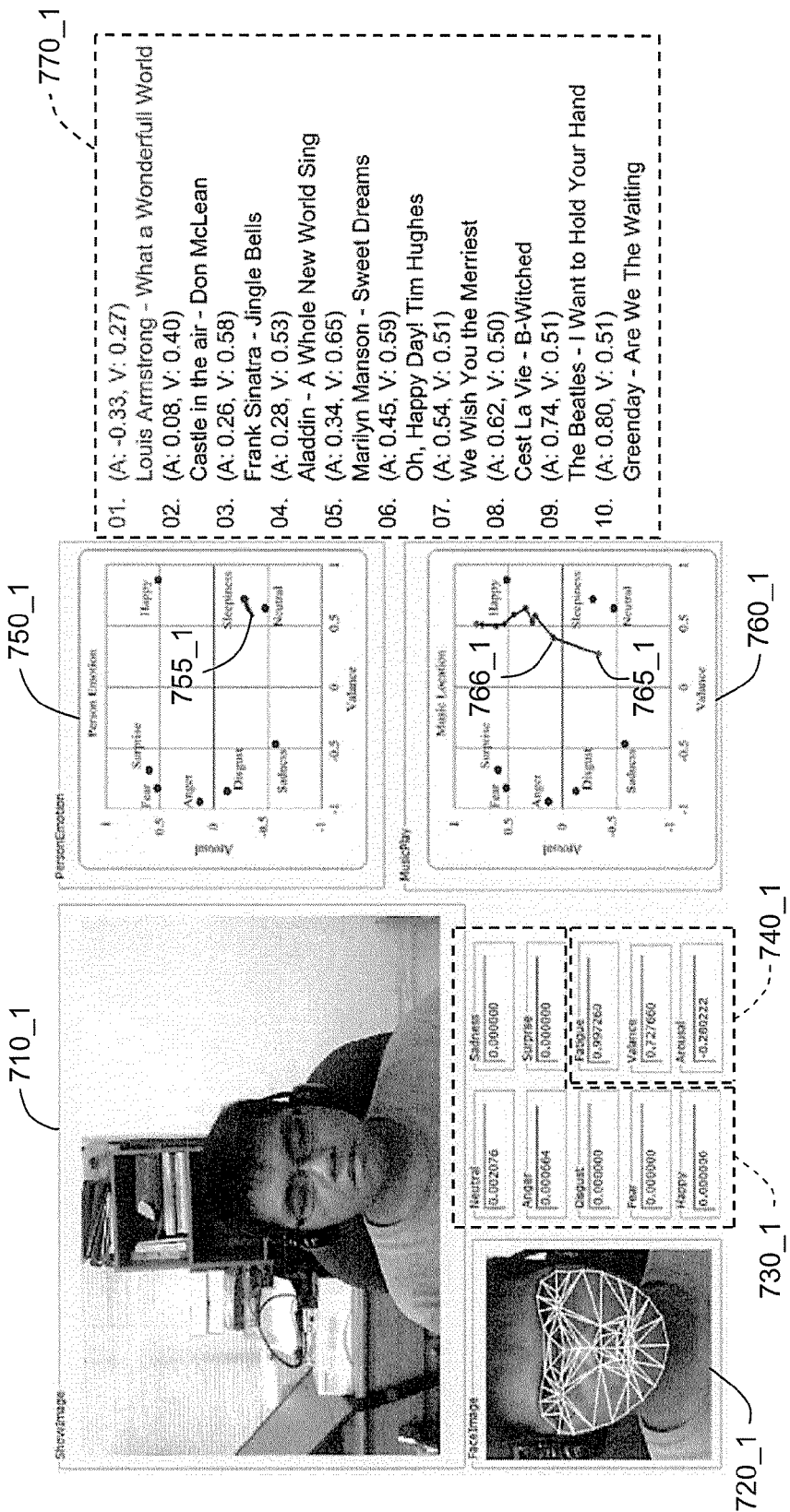
FIG. 7A-FIG. 7D are schematic diagrams of directing an emotion state of a user from tired to happy through songs according to an embodiment of the invention.

FIG. 7A-FIG. 7D are schematic diagrams of directing the emotion state of the user from tired to happy through songs according to an embodiment of the invention. Referring to FIG. 7A, an image 710_1 is, for example, an image captured by the image capturing device 110, and an image 720_1 is, for example, a human face image. Various nodes shown in the image 720_1 are characteristic points used by the image processing device 120 for recognizing the emotion state, and the image processing device 120 can calculate the aforementioned distance characteristic and the displacement characteristic according to lengths of connection lines between the characteristic points and displacement status of the characteristic points.

A region 730_1 records components of 8 predetermined emotions corresponding to the image 720_1. In the present embodiment, the 8 predetermined emotions are, for example, neutral, anger, disgust, fear, happy, sadness, pleasant surprise and fatigue. The component of each predetermined emotion can be represented by a corresponding value. For example, in the present embodiment, the component corresponding to the neutral emotion of the image 720_1 is, for example, 0.002076, and the component corresponding to the anger emotion of the image 720_1 is, for example, 0.000665. The components of the other emotions can be deduced by analogy, which are not repeated. Based on various values shown in the region 730_1, the image processing device 120 can correspondingly calculate the V-value (i.e. the valence) and the A-value (i.e. the arousal) corresponding to the image 720_1.

A region 740_1 records the V-value and the A-value corresponding to the image 720_1. Therefore, according to the region 740_1, it is known that the V-value and the A-value corresponding to the image 720_1 are respectively 0.727660 and −0.280222. Namely, the emotion of the user in the image 720_1 is close to a fatigue state.

An emotion coordinate graph 750_1, for example, records the current emotion coordinates of the user. In the present embodiment, the emotion coordinate graph 750_1 displays the current emotion coordinates corresponding to the predetermined emotions. Moreover, based on the values recorded in the region 740_1, the control device 130 can display a current emotion coordinate 755_1 corresponding to the image 720_1 on the emotion coordinate graph 750_1 based on the V-value and the A-value recorded in the region 740_1.

The emotion coordinate graph 760_1, for example, records the song emotion coordinates corresponding to the songs to be played, and a song playlist 770_1 records names of the songs to be played and the corresponding V-values and the A-values thereof. Taking a first song in the song playlist 770_1 as an example, the name thereof is "Louis Armstrong—What a Wonderful World", and the corresponding V-value and the A-value thereof are respectively 0.27 and −0.33. Therefore, the control device 130 accordingly displays the song emotion coordinate 765_1 corresponding to such song in the emotion coordinate graph 760_1. Taking a second song in the song playlist 770_1 as an example, the name thereof is "Castle in the air—Don McLean", and the corresponding V-value and the A-value thereof are respectively 0.40 and −0.08. Therefore, the control device 130 accordingly displays the song emotion coordinate 766_1 corresponding to such song in the emotion coordinate graph 760_1. The song emotion coordinates on the emotion coordinate graph 760_1 corresponding to the other songs in the song playlist 770_1 can be deduced by analogy, which are not repeated.

In the present embodiment, it is assumed that the playing device 140 is playing the first song in the song playlist 770_1, and the user's emotion (i.e. the emotion state) is changed in response to such song. Now, the control device 130 adjusts the song playlist 770_1 into a song playlist 770_2 shown in FIG. 7B in response to the change of the emotion state of the user.

Figure 7B:
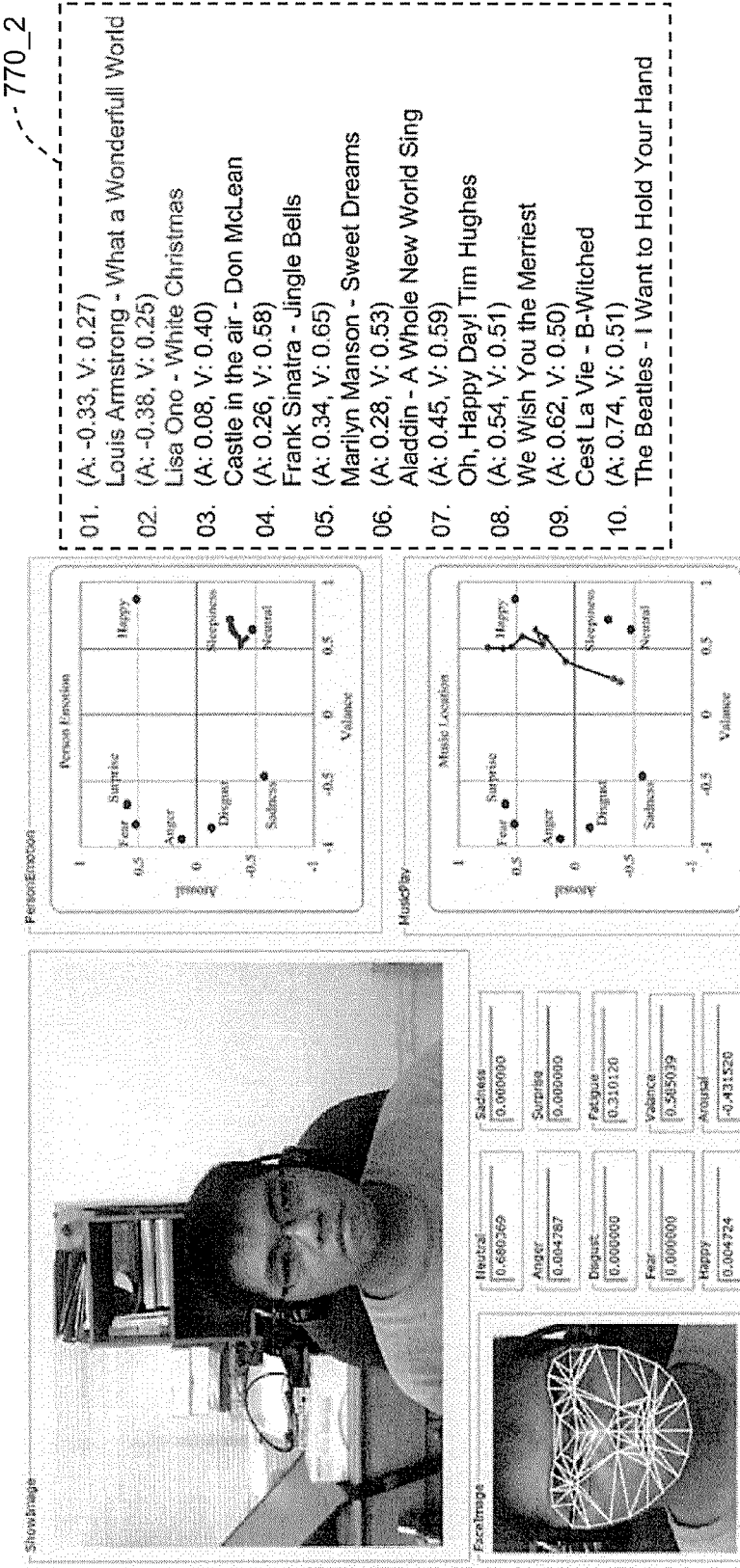

Referring to FIG. 7B, according to the song playlist 770_2, it is known that besides the already played "Louis Armstrong—What a Wonderful World", the second song to the tenth song are all different from the songs in the playlist 770_1. Similarly, it is assumed that the playing device 140 is playing the second song in the song playlist 770_2 (i.e. "Lisa Ono—White Christmas"), and the user's emotion (i.e. the emotion state) is changed in response to such song. Now, the control device 130 adjusts the song playlist 770_2 into a song playlist 770_3 shown in FIG. 7C in response to the change of the emotion state of the user.

Figure 7C:
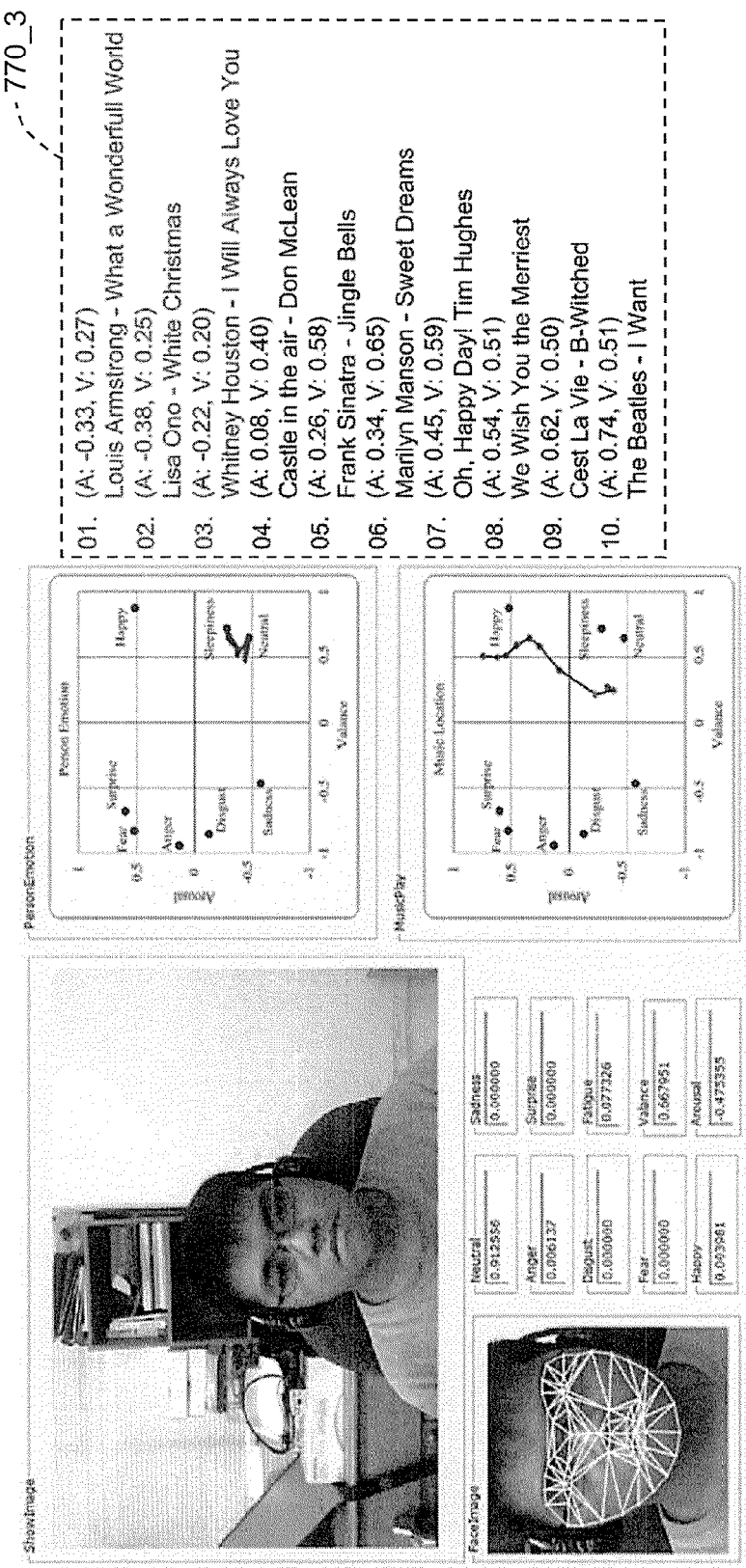

Referring to FIG. 7C, according to the song playlist 770_3, it is known that besides the already played "Louis Armstrong—What a Wonderful World", and "Lisa Ono—White Christmas", the third song to the tenth song are all different from the songs in the playlist 770_2. Similarly, it is assumed that the playing device 140 is playing the third song in the song playlist 770_3 (i.e. "Whitney Houston—I Will Always Love You"), and the user's emotion (i.e. the emotion state) is changed in response to such song. Now, the control device 130 adjusts the song playlist 770_3 into a song playlist 770_4 shown in FIG. 7D in response to the change of the emotion state of the user.

Figure 7D:
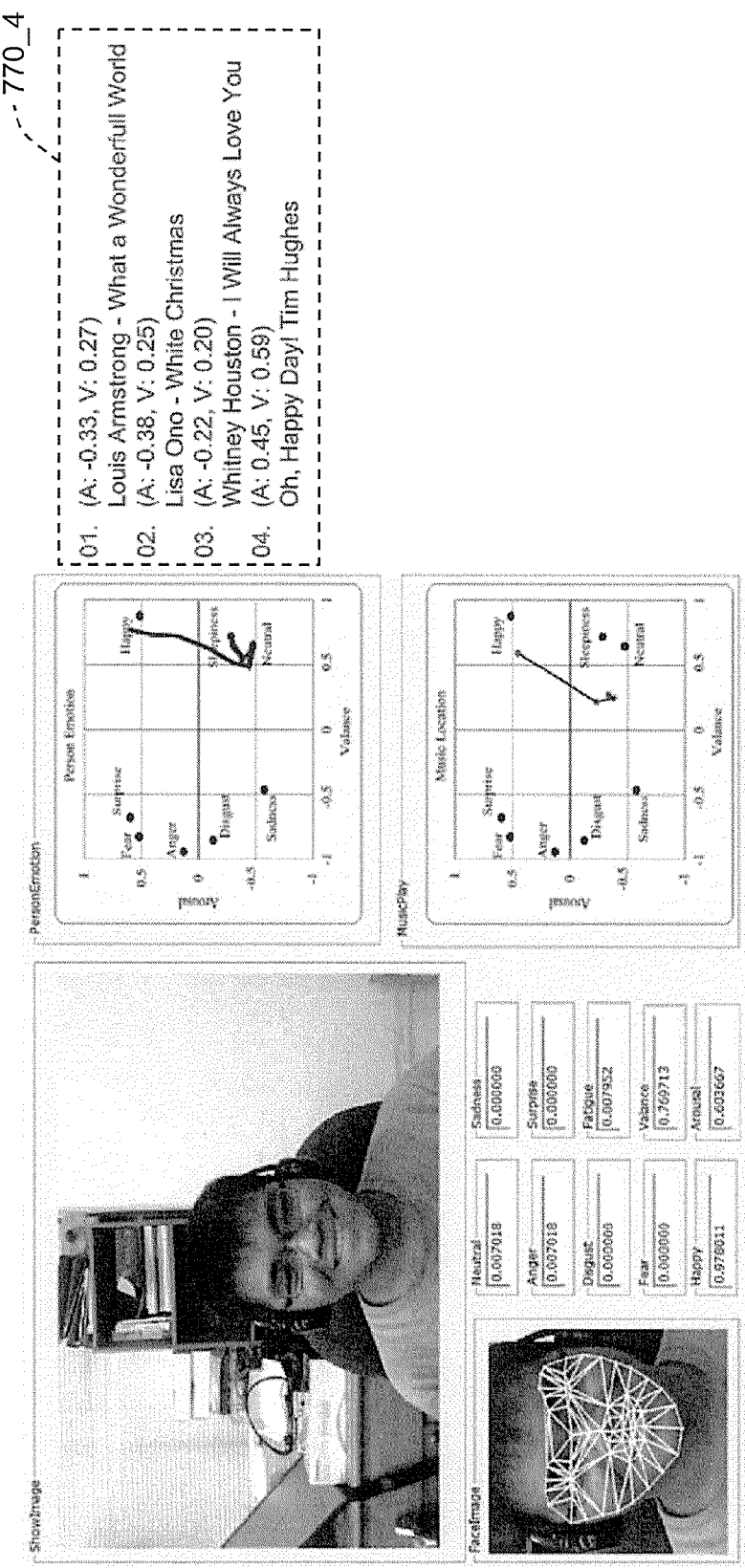

Referring to FIG. 7D, it should be noticed that when the playing device 140 plays the fourth song (i.e. "Oh, Happy Day! Tim Hughes") in the song playlist 770_4, the emotion state of the user has been successfully directed to the target emotion state (i.e. happy).

Taking FIG. 8A to FIG. 8D as an example, FIG. 8A-FIG. 8D are schematic diagrams of directing the emotion state of the user from angry to happy through songs according to an embodiment of the invention. It should be noticed that various images, regions and the meaning of the emotion coordinate graph in FIG. 8A to FIG. 8D are the same to that in FIG. 7A to FIG. 7D, which are not repeated.

Figure 8A:
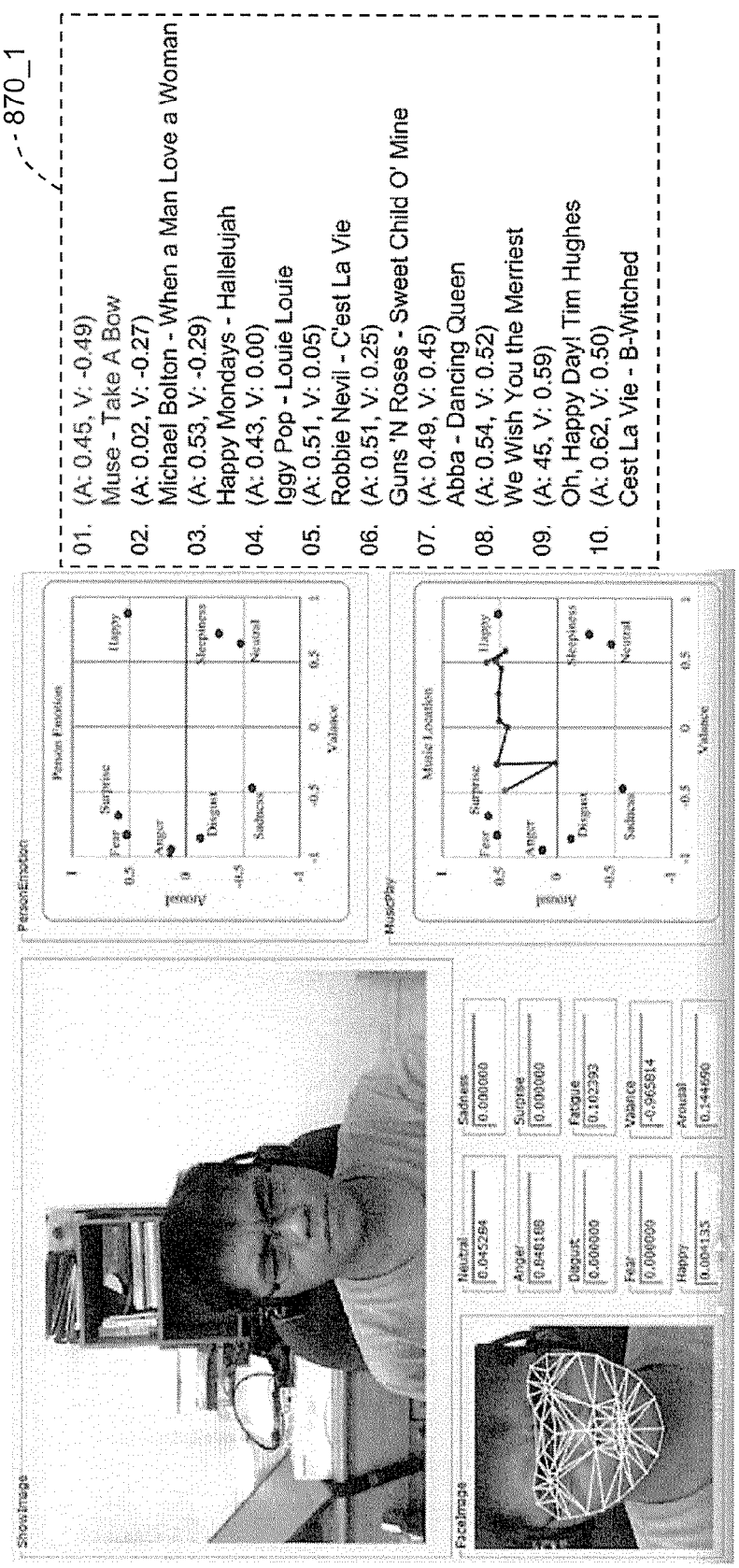
FIG. 8A-FIG. 8D are schematic diagrams of directing an emotion state of a user from angry to happy through songs according to an embodiment of the invention.

Referring to FIG. 8A, it is assumed that the playing device 140 is playing a first song (i.e. "Muse—Take A Bow") in a song playlist 870_1, and the user's emotion (i.e. the emotion state) is changed in response to such song. Now, the control device 130 adjusts the song playlist 870_1 into a song playlist 870_2 shown in FIG. 8B in response to the change of the emotion state of the user.

Figure 8B:
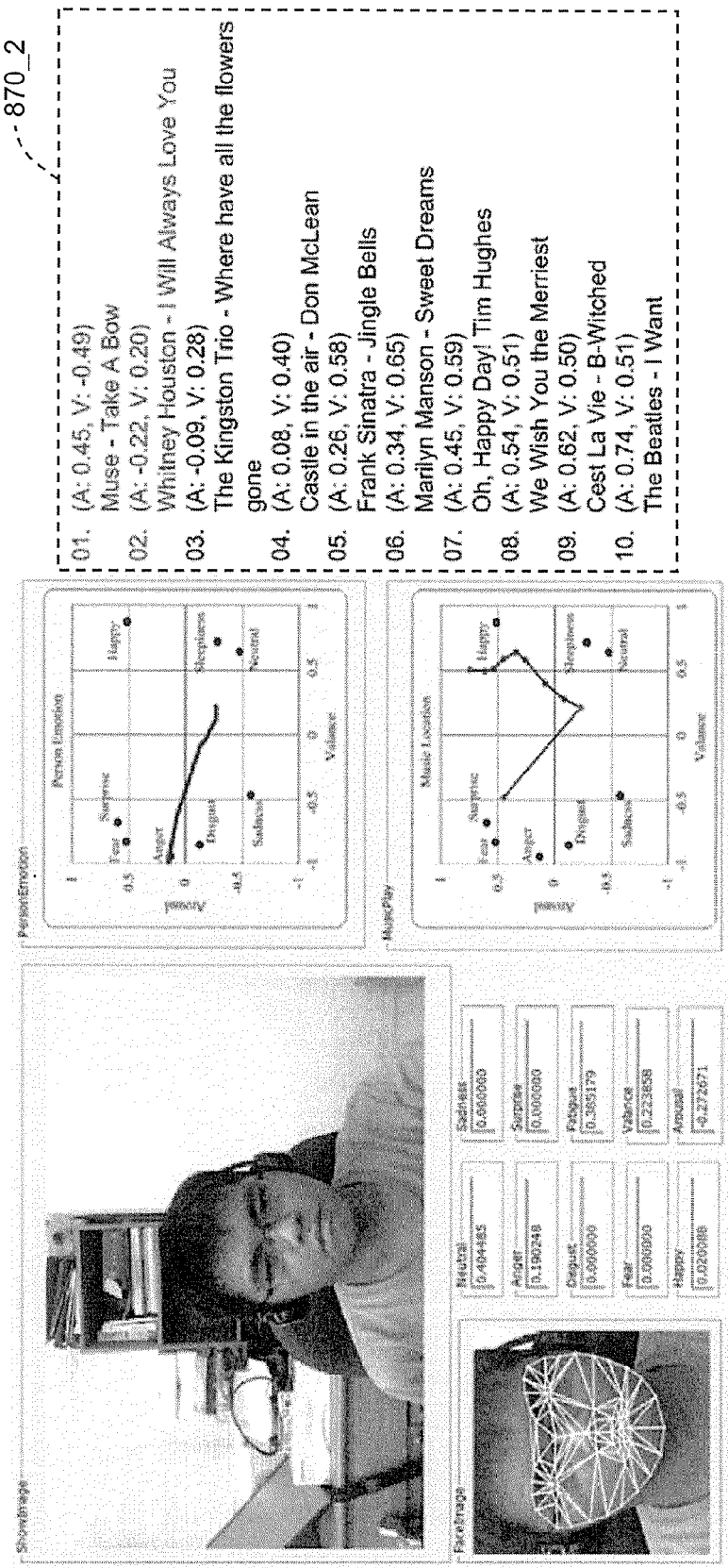

Referring to FIG. 8B, according to the song playlist 870_2, it is known that besides the already played "Muse—Take A Bow", a second song to a tenth song are all different from the songs in the playlist 870_1. Similarly, it is assumed that the playing device 140 is playing the second song in the song playlist 870_2 (i.e. "Michael Bolton—When a Man Love a Woman"), and the user's emotion (i.e. the emotion state) is changed in response to such song. Now, the control device 130 adjusts the song playlist 870_2 into a song playlist 870_3 shown in FIG. 8C in response to the change of the emotion state of the user.

Figure 8C:
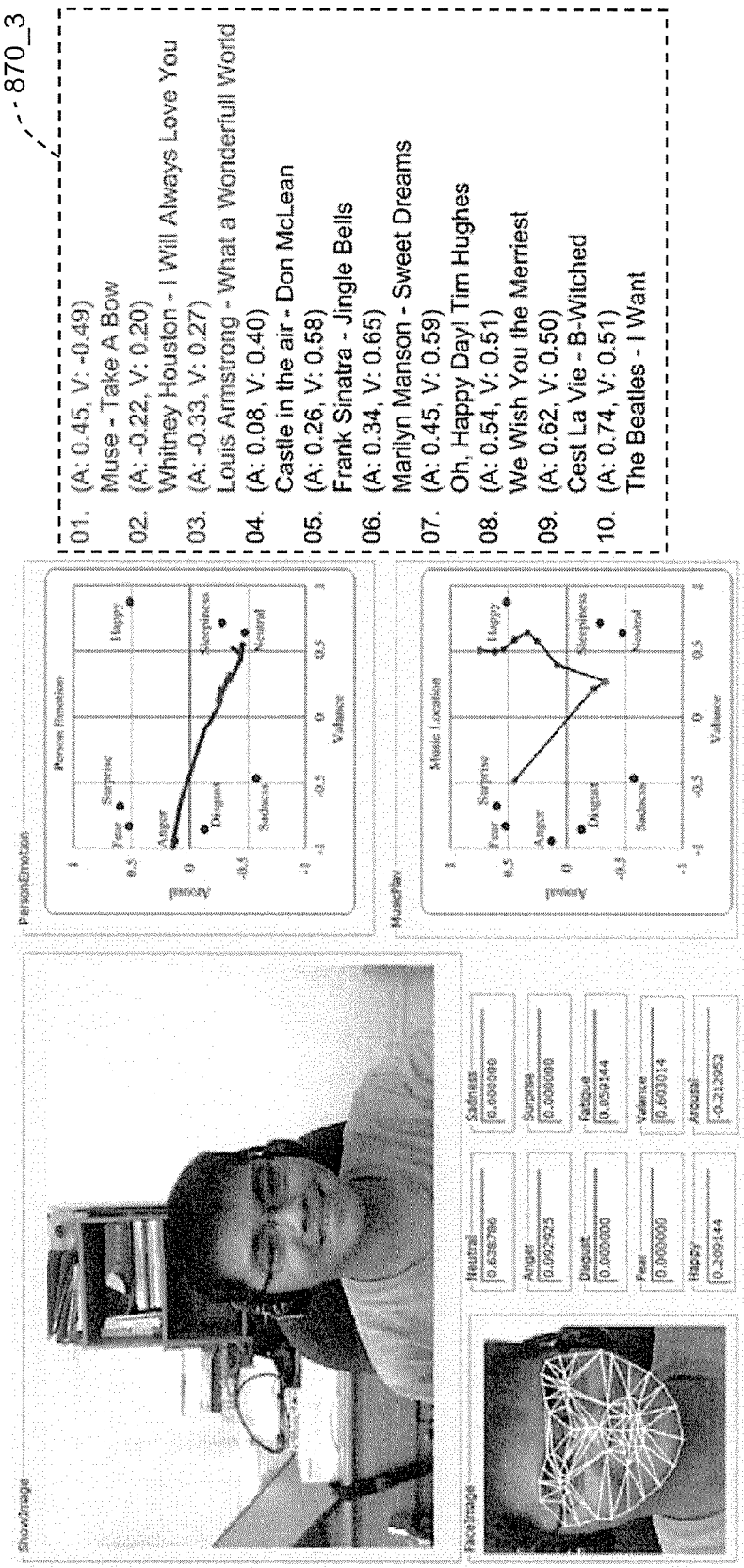

Referring to FIG. 8C, according to the song playlist 870_3, it is known that besides the already played "Muse—Take A Bow", and "Michael Bolton—When a Man Love a Woman", the third song to the tenth song are all different from the songs in the playlist 870_2. Similarly, it is assumed that the playing device 140 is playing the third song in the song playlist 870_3 (i.e. "Louis Armstrong—What a Wonderful World"), and the user's emotion (i.e. the emotion state) is changed in response to such song. Now, the control device 130 adjusts the song playlist 870_3 into a song playlist 870_4 shown in FIG. 8D in response to the change of the emotion state of the user.

Figure 8D:
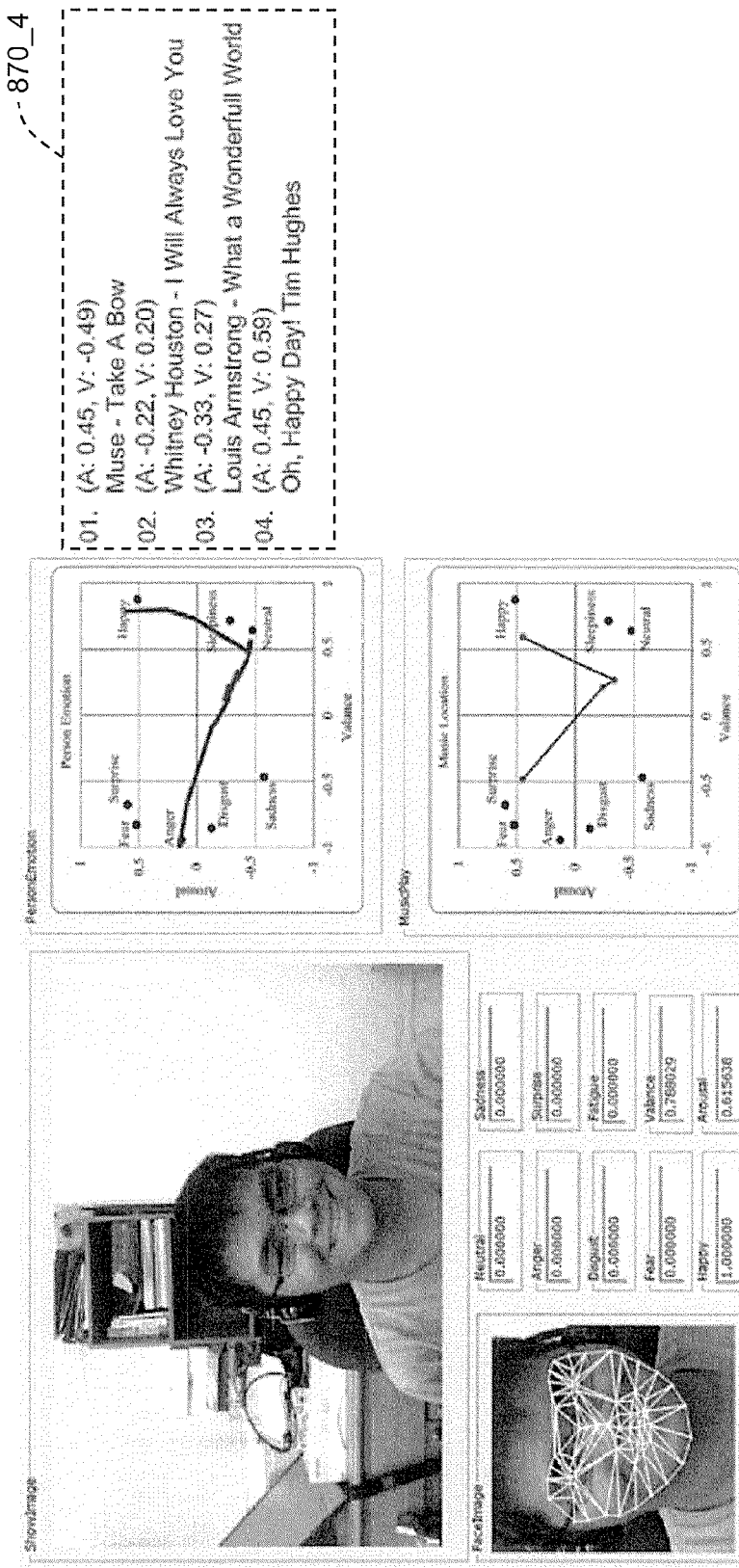

Referring to FIG. 8D, it should be noticed that when the playing device 140 plays the fourth song (i.e. "Oh, Happy Day! Tim Hughes") in the song playlist 870_4, the emotion state of the user has been successfully directed to the target emotion state (i.e. happy).

In this way, the method for selecting music based on face recognition of the invention can gradually direct the emotion state of the user to the target emotion state by constantly updating the songs to be played in the song playlist.

In other embodiments, the music selecting system 100 can be implemented in a means of transportation to direct an emotion state of a driver to a preferred target emotion state (for example, happy) by adjusting a song playlist. In detail, when the driver has a poor emotion state, a driving behaviour thereof is probably affected greatly. For example, when the driver is in an emotion state of fatigue or anger, the probability of a traffic accident is accordingly enhanced. Now, the method for selecting music based on face recognition and the music selecting system 100 of the invention can suitably adjust the songs to be played in the song playlist to gradually direct the emotion state of the driver to a preferred target emotion state, so as to effectively avoid occurrence of the traffic accident.

Figure 9:
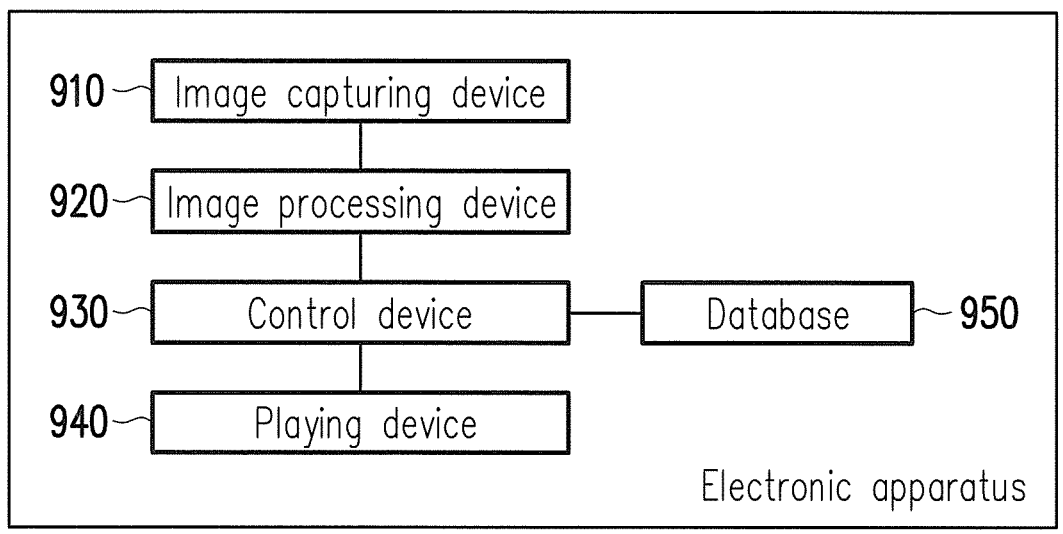
FIG. 9 is a functional block diagram of an electronic apparatus according to an embodiment of the invention.

FIG. 9 is a functional block diagram of an electronic apparatus according to an embodiment of the invention. In the present embodiment, the electronic apparatus 900 includes an image capturing device 910, an image processing device 920, a control device 930, a playing device 940 and a database 950. The image capturing device 910 is connected to the image processing device 920. The control device 930 is connected to the image processing device 920, the playing device 940 and the database 950.

Various possible implementations of the image capturing device 910, the image processing device 920, the control device 930, the playing device 940 and the database 950 may refer to related descriptions of FIG. 1. Moreover, the electronic apparatus 900 can also execute various steps shown in FIG. 2, and details thereof may refer to instructions of the aforementioned embodiment, which are not repeated.

In summary, according to the method for selecting music based on face recognition, the music selecting system and the electronic apparatus of the invention, after the emotion state is recognized based on the human face image, the songs to be played to the user are controlled by adjusting the song playlist, so as to gradually direct the emotion state (for example, nervous, tired, angry and sad, etc.) of the user to the target emotion state (for example, relax, happy and pleased, etc.).

Moreover, according to the method for selecting music based on face recognition, the music selecting system and the electronic apparatus of the invention, the human face images of the user can be repeatedly captured to track the emotion states of the user, so as to adaptively update the songs to be played in the song playlist according to the emotion state recognized each time. In other words, when the emotion state of the user is changed, the songs to be played in the song playlist is adaptively adjusted other than a situation that the songs to be played are not varied after the song playlist is generated.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A method for selecting music based on face recognition, adapted to a music selecting system comprising an image capturing device, an image processing device, a control device, a playing device and a database, the method for selecting music based on face recognition comprising:

accessing, by the control device, the database to retrieve a plurality of song emotion coordinates corresponding to a plurality of songs;

mapping, by the control device, the song emotion coordinates to an emotion coordinate graph;

capturing, by the image capturing device, a human face image;

recognizing, by the image processing device, an emotion state corresponding to the human face image, and transforming the emotion state to a current emotion coordinate;

mapping, by the control device, the current emotion coordinate to the emotion coordinate graph;

updating, by the control device, a song playlist according to a relative position between the current emotion coordinate and a target emotion coordinate, wherein the song playlist comprises a plurality of songs to be played that direct the current emotion coordinate to the target emotion coordinate; and playing, by the playing device, the plurality of songs of the updated song playlist, wherein the step of updating the song playlist according to the relative position between the current emotion coordinate and the target emotion coordinate comprises:

defining, by the control device, a plurality of reference emotion coordinates on a first connection line, wherein the first connection line is connected between the current emotion coordinate and the target emotion coordinate, the plurality of reference emotion coordinates are different from the current emotion coordinate and the target emotion coordinate;

selecting, by the control device, a plurality of candidate song emotion coordinates closest to the reference emotion coordinates from the song emotion coordinates; and setting, by the control device, the songs corresponding to the candidate song emotion coordinates to be the songs to be played, wherein the step of defining the reference emotion coordinates on the first connection line comprises:

characterizing, by the control device, an nth reference emotion coordinate in the reference emotion coordinates as:

$$A_E^n = A_S + \frac{d_{TS}}{N_R} \times \sin(\theta_{TS}) \times n,$$

$$V_E^n = V_S + \frac{d_{TS}}{N_R} \times \cos(\theta_{TS}) \times n$$

wherein NR is a total number of the songs to be played, n is a positive integer between 1 and NR, dTS is a distance between the emotion coordinate and the target emotion coordinate, θTS is an included angle between a horizontal axis of the emotion coordinate graph and the first connection line, $A_E^n$ is a vertical coordinate of the nth reference emotion coordinate on the emotion coordinate graph, $V_E^n$ is a horizontal coordinate of the nth reference emotion coordinate on the emotion coordinate graph, AS is a vertical coordinate of the current emotion coordinate on the emotion coordinate graph, and VS is a horizontal coordinate of the current emotion coordinate on the emotion coordinate graph.

2. The method for selecting music based on face recognition as claimed in claim 1, wherein an nth candidate song emotion coordinate in the candidate song emotion coordinates satisfies a following equation:

$$(V_M^n, A_M^n) = \arg \min_{V_M, A_M} \left( \sqrt{(V_E^n - V_M)^2 + (A_E^n - A_M)^2} \times w \right)$$

wherein $A_M^n$ is a vertical coordinate of an nth candidate song emotion coordinate on the emotion coordinate graph, $V_M^n$ is a horizontal coordinate of the nth candidate song emotion coordinate on the emotion coordinate graph, $$w = \frac{1}{\cos(\theta_{EM}) + 2},$$

θEM is an included angle between a second connection line and a third connection line, wherein the second connection line is connected between the nth reference emotion coordinate and the target emotion coordinate, and the third connection line is connected between the nth reference emotion coordinate and the nth candidate song emotion coordinate.

3. The method for selecting music based on face recognition as claimed in claim 2, wherein after the step of updating the song playlist according to the relative position between the current emotion coordinate and the target emotion coordinate, the method further comprises:
   playing, by the playing device, the songs to be played according to the song playlist.

4. The method for selecting music based on face recognition as claimed in claim 3, wherein after the step of playing the songs to be played according to the song playlist, the method further comprises:
   repeating the steps of capturing the human face image, recognizing the emotion state corresponding to the human face image, mapping the current emotion coordinate to the emotion coordinate graph and updating the song playlist according to the relative position between the current emotion coordinate and the target emotion coordinate until the current emotion coordinate is directed to the target emotion coordinate or playing of the songs to be played is finished.

5. A music selecting system, comprising:
   an image capturing device;
   an image processing device, connected to the image capturing device;
   a control device, connected to the image processing device;
   a playing device, connected to the control device; and
   a database, connected to the control device,
   wherein the control device accesses the database to retrieve a plurality of song emotion coordinates corresponding to a plurality of songs,
   the control device maps the song emotion coordinates to an emotion coordinate graph,
   the image capturing device captures a human face image,
   the image processing device recognizes an emotion state corresponding to the human face image, and transforms the emotion state to a current emotion coordinate,
   the control device maps the current emotion coordinate to the emotion coordinate graph,
   the control device updates a song playlist according to a relative position between the current emotion coordinate and a target emotion coordinate, wherein the song playlist comprises a plurality of songs to be played that direct the current emotion coordinate to the target emotion coordinate, and
   the playing device plays the plurality of songs of the updated song playlist,
   wherein the operation of updating the song playlist according to the relative position between the current emotion coordinate and the target emotion coordinate comprises:
   the control device defines a plurality of reference emotion coordinates on a first connection line, wherein the first connection line is connected between the current emotion coordinate and the target emotion coordinate, the plurality of reference emotion coordinates are different from the current emotion coordinate and the target emotion coordinate,
   the control device selects a plurality of candidate song emotion coordinates closest to the reference emotion coordinates from the song emotion coordinates, and
   the control device sets the songs corresponding to the candidate song emotion coordinates to be the songs to be played,
   wherein the operation of defining the reference emotion coordinates on the first connection line comprises:
   the control device characterizes an nth reference emotion coordinate in the reference emotion coordinates as:

$$A_E^n = A_S + \frac{d_{TS}}{N_R} \times \sin(\theta_{TS}) \times n,$$

$$V_E^n = V_S + \frac{d_{TS}}{N_R} \times \cos(\theta_{TS}) \times n$$

wherein NR is a total number of the songs to be played, n is a positive integer between 1 and NR, dTS is a distance between the emotion coordinate and the target emotion coordinate, θTS is an included angle between a horizontal axis of the emotion coordinate graph and the first connection line, $A_E^n$ is a vertical coordinate of the nth reference emotion coordinate on the emotion coordinate graph, $V_E^n$ is a horizontal coordinate of the nth reference emotion coordinate on the emotion coordinate graph, AS is a vertical coordinate of the current emotion coordinate on the emotion coordinate graph, and VS is a horizontal coordinate of the current emotion coordinate on the emotion coordinate graph.

6. The music selecting system as claimed in claim 5, wherein an nth candidate song emotion coordinate in the candidate song emotion coordinates satisfies a following equation:

$$(V_M^n, A_M^n) = \arg \min_{V_M, A_M} \left( \sqrt{(V_E^n - V_M)^2 + (A_E^n - A_M)^2} \times w \right)$$

wherein $A_M^n$ is a vertical coordinate of an nth candidate song emotion coordinate on the emotion coordinate graph, $V_M^n$ is a horizontal coordinate of the nth candidate song emotion coordinate on the emotion coordinate graph, $$w = \frac{1}{\cos(\theta_{EM}) + 2},$$

$\theta_{EM}$ is an included angle between a second connection line and a third connection line, wherein the second connection line is connected between the nth reference emotion coordinate and the target emotion coordinate, and the third connection line is connected between the nth reference emotion coordinate and the nth candidate song emotion coordinate.

7. The music selecting system as claimed in claim 6, wherein the playing device plays the songs to be played according to the song playlist.

* * * * *